United States Patent
Lazarevski et al.

(10) Patent No.: US 6,593,360 B1
(45) Date of Patent: Jul. 15, 2003

(54) 8A- AND 9A-15-MEMBERED LACTAMS

(75) Inventors: Gorjana Lazarevski, Zagreb (HR); Sulejman Alihodžić, Zagreb (HR); Gabrijela Kobrehel, Zagreb (HR); Stjepan Mutak, Zagreb (HR)

(73) Assignee: Pliva, farmaceutska industrija, dionicko drustvo, Zagreb (HR)

(*) Notice: Subject to any disclaimer, the term of this patent is extended or adjusted under 35 U.S.C. 154(b) by 0 days.

(21) Appl. No.: 09/959,204

(22) PCT Filed: Apr. 19, 2000

(86) PCT No.: PCT/HR00/00009
§ 371 (c)(1),
(2), (4) Date: Jan. 22, 2002

(87) PCT Pub. No.: WO00/63223
PCT Pub. Date: Oct. 26, 2000

(30) Foreign Application Priority Data

Apr. 20, 1999 (HR) .......................................... P990116A

(51) Int. Cl.$^7$ .......................... C07H 17/08; A61K 31/70
(52) U.S. Cl. ..................... 514/460; 540/454; 540/455
(58) Field of Search ............................. 540/454, 455; 514/460

(56) References Cited

U.S. PATENT DOCUMENTS 6,110,965 A * 8/2000 Lazarevski et al. ......... 514/459

* cited by examiner

Primary Examiner—Bruck Kifle
(74) Attorney, Agent, or Firm—Connolly Bove Lodge & Hutz LLP

(57) ABSTRACT

The invention relates to novel 15-membered 8a- and 9a-lactams from the class of 6-O-methyl-erythromycin A of general formula (I)

their pharmaceutically acceptable addition salts with inorganic or organic acids and their hydrates, to intermediates for their preparation, to a process for their preparation, to their pharmaceutically acceptable addition salts with inorganic or organic acids, to their hydrates, to a process for the preparation of pharmaceutical compositions as well as to a use of pharmaceutical compositions for the treatment of bacterial infections.

62 Claims, No Drawings

8A- AND 9A-15-MEMBERED LACTAMS

TECHNICAL FIELD OF THE INVENTION
A61K 31/70, C07H 17/08

TECHNICAL PROBLEM

The invention relates to novel 15-membered 8a- and 9a-lactams from the class of the macrolide antibiotic 6-O-methyl-erythromycin A, to intermediates for their preparation, to a process for their preparation, to their pharmaceutically acceptable addition salts with inorganic and organic acids, to their hydrates, to a process for the preparation of pharmaceutical compositions as well as to the use of pharmaceutical compositions for treatment of bacterial infections.

PRIOR ART

Erythromycin A is a macrolide antibiotic, whose structure is characterized by a 14-membered lactone ring with C-9 ketone and two sugars, L-cladinose and D-desosamine, glycosidically bound in C-3 and C-5 positions onto an aglycone moiety of the molecule (McGuire, Antibiot. Chemother. 1952; 2:281). By an oximation of C-9 ketone with hydroxylamine hydrochloride, by Beckmann rearrangement of the obtained 9(E)-oxime and by a reduction of the formed 6,9-imino ether there is obtained 9-deoxo-9a-aza-9a-homoerythromycin A, the first semisynthetic macrolide with a 15-membered azalactone ring (Kobrehel G. et al., U.S. Pat. No. 4,328,334, 5/1982). By means of a reductive methylation of 9a-amino group, azithromycin, a prototype of a novel class of 9a-azalide antibiotics was synthesized (Kobrehel G. et al., BE 892 357, 7/1982). In addition to having a broad antimicrobial spectrum including also Gram-negative bacteria, azithromycin is also characterized by a long biological half-life, a specific transport mechanism to the site of use and a short therapy time. Azithromycin easily penetrates and accumulates inside human fagocyte cells resulting in improved activity on intracellular pathogenic microorganisms, from classes Legionella, Chlamydia and Helicobacter.

It is known as well that by a O-methylation of C-6 hydroxyl group clarithromycin (6-O-methyl-erhytromycin A) is obtained (Morimoto S. et al., J. Antibiotics 1984. 37. 187). In relation to erythromycin A, clarithromycin is much more stable in acidic medium and exhibits improved in vitro activity against Gram-positive bacterial strains (Kirst H. A. et al., Antimicrobial Agents and Chemother., 1989, 1419).

By recent research on 14-membered macrolides, a novel type of macrolide antibiotics. ketolides, has been discovered, whose structure is characterized by a 3-keto croup instead of a neutral sugar, L-cladinose (Agouridas C. et al., EP 596802 A1 5/1994; Le Martret O., FR 2697524 A1 5/94). Ketolides exhibit significantly improved in vitro activity against MLS (macrolide, lincosamide and streptogramin B) induced-resistant organisms (Jamjian C., Antimicrob. Agents Chemother., 1997, 41, 485).

It has been described as well that by Beckmann rearrangement of 6-O-methyl-erythromycin A 9(E)- and 9(Z)-oximes, hydrolysis of cladinose of the obtained 8a- and 9a-lactams, protection of 2'-hydroxyl group of desosamine, an acylation reaction, an oxidation of 3-hydroxyl group and by deprotection, there are obtained 15-membered 8a- and 9a-ketolides from the class of 6-O-methyl-erythromycin A (Lazarevski G. et al., PCT/HR 99/00004, 4/99).

According to known and established prior art, novel 15-membered 8a- and 9a-lactams from the class of 6-O-methyl-erythromycin A, which are the object of the present invention, their pharmaceutically acceptable addition salts with organic or inorganic acids, their hydrates, methods and intermediates for their preparation and methods for their preparation and use as pharmaceutical preparations have hitherto not been described. The object of this invention is preparation of 11,12-substituted derivatives of 6-O-methyl-erythromycin A 8a- and 9a-lactams and their 3-hydroxy and 3-keto derivatives. A further object of the present invention are 3-acyl derivatives of 6-O-methyl-erythromycin A 8a- and 9a-lactams and 3-acyl-derivatives of 11,12-substituted 6-O-methyl-erythromycin A 8a- and 9a-lactams. Novel 15-membered 8a- and 9a-lactams of the present invention are potential antibiotics for the treatment of Gram-positive and Gram-negative susceptible resistant strains.

DESCRIPTION OF TECHNICAL PROBLEMS WITH EXAMPLES

Novel 15-membered 8a- and 9a-lactams from the class of 6-O-methyl-erythromycin A of the general formula (I)

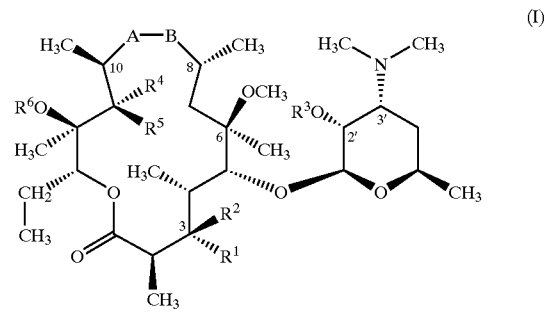

(I)

their pharmaceutically acceptable addition salts with inorganic or organic acids and their hydrates, wherein A stands for NH group and B simultaneously stands for C=O group, or A stands for C=O group and B simultaneously stands for NH group, $R^1$ stands for OH group, L-cladinosyl group of formula (II)

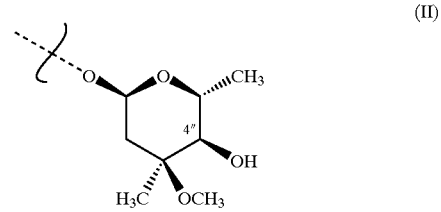

(II)

or $R^1$ stands for a group of formula (III),

(III)

wherein

Y stands for hydrogen, $C_1$–$C_6$ alkyl, $C_1$–$C_6$ alkyl group with at least one incorporated O, N or S atom or Y stands for $(CH_2)_n$—Ar, wherein $(CH_2)_n$ stands for alkyl and n stands for 1–10, with or without incorporated O, N or S atoms, and Ar stands for 5–10-membered monocyclic or bicyclic aromatic ring containing 0–3 O, N or S atoms, which is unsubstituted or substituted with 1–3 groups representing halogen, OH, OMe, $NO_2$, $NH_2$, amino-$C_1$–$C_3$ alkyl, amino-$C_1$–$C_3$ dialkyl, CN, $SO_2NH_2$, $C_1$–$C_3$ alkyl, or $R^1$ together with $R^2$ stands for ketone, $R^2$ stands for hydrogen or together with $R^1$ stands for ketone, $R^3$ stands for hydrogen or $C_1$–$C_4$ alkanoyl group, $R^4$ stands for hydrogen or together with $R^5$ stands for ketone, $R^5$ stands for OH, $NH_2$, amino-$C_1$–$C_3$ alkyl or amino-$C_1$–$C_3$ dialkyl, $O(CH_2)_nAr$ or $S(CH_2)_nAr$, wherein $(CH_2)_n$ and Ar have the above meanings, or together with $R^4$ stands for ketone, $R^6$ stands for hydrogen, $C_1$–$C_6$ alkyl, $C_1$–$C_6$ alkyl group with at least one incorporated O, N or S atom, or $(CH_2)_n$—Ar group, wherein $(CH_2)_n$ and Ar have the above meanings, or $R^5$ and $R^6$ together with intervening atoms form an additional ring of formula (IV)

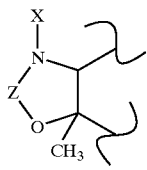

(IVa)

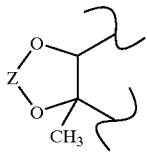

(IVb)

wherein

Z stands for $CH_2$, C=O, C(NH), SO, $SO_2$, $CH_2CO$, $COCH_2$, $CH_2CH_2CO$. $COCH_2CH_2$ or $CH_2CH_2$, and X stands for hydrogen, $C_1$–$C_3$ alkyl, $NH_2$, amino-$C_1$–$C_3$ alkyl or amino-$C_1$–$C_3$ dialkyl or $(CH_2)_n$—Ar group, wherein $(CH_2)_n$ and Ar have the above meanings, are obtained as follows:

Step 1:

The first step of the invention includes a reaction of 6-O-methyl-9a-aza-9a-homo-erythromycin A or 6-O-methyl-8a-aza-8a-homoerythromycin A, obtained according to PCT/HR 99/00004, 4/99, with ethylene carbonate in the presence of inorganic or organic bases, preferably potassium carbonate, in a reaction-inert solvent, preferably in ethyl acetate, yielding corresponding 11,12-cyclic carbonates of the general formula (I), wherein A stands for NH and B simultaneously stands for C=O group, or A stands for C=O group and B simultaneously stands for NH group, $R^1$ stands for L-cladinosyl group of formula (II) and $R^2$, $R^3$ and $R^4$ are mutually the same and stand for hydrogen, $R^5$ and $R^6$ together with intervening atoms form an additional ring of formula (IVb), wherein Z stands for C=O group.

Step 2:

11,12-cyclic carbonates obtained in the Step 1, are subjected to hydrolysis with strong acids, preferably with 0.25–1.5 N hydrochloric acid, in a mixture of water and lower alcohols, preferably methanol, ethanol or isopropanol, over 10–30 hours at room temperature, yielding 3-decladinosyl derivatives of general formula (I), wherein A stands for NH group and B simultaneously stands for C=O group, or A stands for C=O group and B simultaneously stands for NH group, $R^1$ stands for OH group, $R^2$, $R^3$ and $R^4$ are mutually the same and stand for hydrogen, and $R^5$ and $R^6$ together with intervening atoms form an additional ring of formula (IVb), wherein Z stands for C=O group.

Step 3:

3-Decladinosyl derivatives from the Step 2 are subjected to a selective acylation of the hydroxyl group in 2'-position. Acylation is carried out with chlorides or anhydrides of carboxylic acids with up to 4 carbon atoms, preferably with acetic acid anhydride, in the presence of inorganic or organic bases, in a reaction-inert solvent at a temperature from 0–30° C., yielding 2'-O-acyl derivatives of the general formula (I), wherein A stands for NH group and B simultaneously stands for C=O group, or A stands for C=O group and B simultaneously stands for NH group, $R^1$ stands for OH group, $R^2$ and $R^4$ are mutually the same and stand for hydrogen, $R^3$ stands for acetyl and $R^5$ and $R^6$ together with intervening atoms form an additional ring of formula (IVb), wherein Z stands for C=O group.

As suitable bases sodium hydrogen carbonate, sodium carbonate, potassium carbonate, triethylamine, pyridine, tributylamine, preferably sodium hydrogen carbonate are used. As a suitable inert solvent methylene chloride, dichloroethane, acetone, pyridine, ethyl acetate, tetrahydrofuran, preferably methylene chloride is used.

Step 4:

2'-Acetyl derivatives from the Step 3 are optionally subjected to a reaction with mixed anhydrides of carboxylic acids of formula Y—COO—$R^1$, wherein Y stands for hydrogen, $C_1$–$C_6$ alkyl, $C_1$–$C_6$ alkyl group with at least one incorporated O, N or S atom, or Y stands for $(CH_2)_n$—Ar, wherein $(CH_2)_n$ stands for alkyl and n is 1–10, without or with incorporated O, N or S atoms, and Ar stands for 5–10-membered monocyclic or bicyclic aromatic ring comprising 0–3 O, N or S atoms, which is unsubstituted or substituted with 1–3 groups representing halogen, OH, OMe, $NO_2$, $NH_2$, amino-$C_1$–$C_3$ alkyl or amino-$C_1$–$C_3$ dialkyl, CN, $SO_2NH_2$, $C_1$–$C_3$ alkyl and $R^1$ is a group which is usually used for the preparation of mixed anhydrides such as pivaloyl, p-toluenesulfonyl, isobutoxycarbonyl, ethoxycarbonyl or isopropoxycarbonyl group, in the presence of inorganic or organic bases, in a reaction-inert solvent, preferably in methylene chloride, at a temperature from 0–30° C. for 3–100 hours, yielding 3-acyl derivatives of general formula (I), wherein $R^1$ stands for a group of formula (III), wherein Y has the above meanings, A stands for NH group and B simultaneously stands for C=O group, or A stands for C=O group and B simultaneously stands for NH group, $R^2$ and $R^4$ are mutually the same and stand for hydrogen. $R^3$ stands for acetyl and $R^5$ and $R^6$ together with intervening atoms form an additional ring of formula (IVb), wherein Z stands for C=O group, which are subsequently subjected to deprotection with lower alcohols, preferably in methanol, at a temperature from room temperature to the reflux temperature of the solvent, yielding a compound of the general formula (I), wherein $R^3$ stands for hydrogen and all remaining substituents have the above meanings.

Step 5:

2'-Acetyl derivatives from the Step 3 are optionally subjected to oxidation of the hydroxyl group in C-3 position of an aglycone ring according to a modified Moffat-Pfitzner process with N,N-dimethyl aminopropyl-3-ethyl-carbodiimide in the presence of dimethyl sulfoxide and pyridinium trifluoroacetate as a catalyst in an inert organic solvent, preferably in methylene chloride, at a temperature from 10° C. to room temperature, yielding 3-oxo derivatives of the general formula (I), wherein A stands for NH group and B simultaneously stands for C=O group, or A stands for C=O group and B simultaneously stands for NH group, $R^1$ together with $R^2$ stands for ketone, $R^3$ stands for acetyl, $R^4$ stands for hydrogen and $R^5$ and $R^6$ together with intervening atoms form an additional ring of formula (IVb), wherein Z stands for C=O group, which are subsequently subjected to deprotection in lower alcohols, preferably in methanol, at a temperature from room temperature to the reflux temperature of the solvent, yielding a compound of the general formula (I), wherein $R^3$ stands for hydrogen and all remaining substituents have the above meanings.

Step 6:

By subjecting 6-O-methyl-9a-aza-9a-homoerythromycin A or 6-O-methyl-8a-aza-8a-homoerythromycin A obtained according to PCT/HR 99/00004, 4/99, to hydrolysis with strong acids as described in the Step 2, followed by a selective acylation of 2'-position as in the Step 3 and by a reaction with mixed anhydrides as in the Step 4, there are obtained compounds of the general formula (I), wherein $R^1$ has the meaning of a group of the formula (III), wherein Y stands for hydrogen, $C_1$–$C_6$ alkyl, $C_1$–$C_6$ alkyl group with at least one incorporated O, N or S atom, or Y stands for $(CH_2)_n$—Ar, wherein $(CH_2)_n$ stands for alkyl and n stands for 1–10, without or with incorporated O, N or S atoms, and Ar stands for 5–10-membered monocyclic or bicyclic aromatic ring containing 0–3 O, N or S atoms, which is unsubstituted or substituted with 1–3 groups representing halogen, OH, OMe, $NO_2$, $NH_2$, amino-$C_1$–$C_3$-alkyl or amino-$C_1$–$C_3$ dialkyl, CN, $SO_2NH_2$, $C_1$–$C_3$ alkyl, $R^2$, $R^3$, $R^4$, and $R^6$ are mutually the same and stand for hydrogen and $R^5$ is OH group.

Step 7:

By subjecting 6-O-methyl-9a-aza-9a-homoerythromycin A or 6-O-methyl-8a-aza-8a-homoerythromycin A obtained according to PCT/HR 99/00004, 4/99, to hydrolysis with strong acids as described in the Step 2, followed by a selective acylation of 2'-position as in the Step 3 and by oxidation and deprotection as in the Step 5, after purification with low pressure chromatography on a silica gel column using the system ethyl acetate-(n-hexane)-diethyl amine 10:10:2 and by subsequent evaporation of chromatographically homogeneous fractions with lower Rf and rechromatography in the system $CH_2Cl_2$—$CH_3OH$-conc.$NH_4OH$ 90:9:0.5, there is obtained a compound of the general formula (I), wherein A stands for NH group and B simultaneously stands for C=O group or A stands for C=O group and B simultaneously stands for NH group, $R^1$ together with $R^2$ stands for a ketone, $R^3$ and $R^6$ are mutually the same and stand for hydrogen and $R^4$ together with $R^5$ stands for a ketone.

Alternatively, compounds from the Step 4 can be obtained by subjecting the compounds from the Step 6 to a reaction with ethylene carbonate in a manner as described in the Step 1.

Alternatively, the compounds from the Step 2 can be obtained by changing the sequence of the reaction steps in such a manner that 6-O-methyl-9a-aza-9a-homoerythromycin A or 6-O-methyl-8a-aza-8a-homoerythromycin A obtained according to PCT/HR 99/00004, 4/99, are first subjected to a hydrolysis with strong acids as described in the Step 2 and then to a reaction with ethylene carbonate in a manner described in the Step 1.

Alternatively, the compounds of the Step 5 can be obtained in such a manner that 3-decladinosyl-3-oxo-6-O-methyl-9a-aza-9a-homoerythromycin A or 3-decladinosyl-3-oxo-6-O-methyl-8a-aza-8a-homo-erythromycin A obtained according to PCT/HR 99/00004, 4/99, are subjected to a reaction with ethylene carbonate in the manner described in the Step 1.

Pharmaceutically acceptable addition salts which are also an object of the present invention, are obtained by a reaction of novel compounds from the class of 6-O-methyl-9a-aza-9a-homo- and 6-O-methyl-8a-aza-8a-homo-erythromycins A of the general formula (I), wherein A, B, $R^1$, $R^2$, $R^3$, $R^4$, $R^5$ and $R^6$ have the above meanings, with an at least equimolar amount of a suitable corresponding inorganic or organic acid such as hydrochloric, hydroiodic, sulfuric, phosphoric, acetic, propionic, trifluoroacetic, maleic, citric, stearic, succinic, ethylsuccinic, methanesulfonic, benzenesulfonic, p-toluenesulfonic, laurylsulfonic acid and the like, in a reaction-inert solvent. Addition salts are isolated by filtration if they are insoluble in the reaction-inert solvent, by precipitation by means of a non-solvent or by evaporation of the solvent, most frequently by lyophilization.

The process is illustrated by the following examples which do not limit the scope of the invention in any way.

EXAMPLE 1

6-O-Methyl-9a-aza-9a-homoerythromycin A 11,12-Cyclic Carbonate

To ethyl acetate (80 ml) 6-O-methyl-9a-aza-9a-homoerythromycin A (3 g, 0.0039 mole) obtained according PCT/HR 99/00004, 4/99, $K_2CO_3$ (9 g, 0.0651 mole) and ethylene carbonate (9 g, 0.1022 mole) were added and then the reaction mixture was stirred under heating at reflux temperature for 12 hours. The reaction suspension was diluted with ethyl acetate (100 ml) and rinsed with saturated NaCl solution (100 ml) and water (200 ml). The evaporation of the organic solvent gave an oily residue, from which by low-pressure chromatography on a silica gel column using the system $CH_2Cl_2$—$CH_3OH$-conc.$NH_4OH$, 90:9:1.5 the title product (2 g) was obtained.

IR (KBr) cm$^{-1}$ 3452, 2974, 2939, 2833, 2787, 1815, 1737, 1668, 1531, 1456, 1379, 1287, 1168, 1111, 1053, 1014, 955, 903. $^1$H NMR (300 MHz, CDCl$_3$) δ 5.76 (9a-CONH), 5.10 (H-1"), 4.87 (H-13), 4.41 (H-1'), 4.31 (H-10), 4.20 (H-11), 4.03 (H-5"), 3.97 (H-3), 3.65 (H-5), 3.47 (H-5'), 3.34 (3"-OCH$_3$), 3.18 (H-2'), 3.14 (6-OCH$_3$), 3.02 (H-4"), 2.84 (H-2), 2.43 (H-3'), 2.33 (H-2"a), 2.28/3'-N(CH$_3$)$_2$/, 2.19 (H-8), 2.28 (H-7a), 2.19 (H-4), 1.79 (H-14a), 1.65 (H-4'a), 1.57 (H-2"b), 1.56 (H-14b), 1.49 (12-CH$_3$), 1.38 (6-CH$_3$), 1.29 (5"-CH$_3$), 1.27 (H-7b), 1.24 (3"-CH$_3$), 1.21 (5'-CH$_3$), 1.20 (H-4'b), 1.20 (2-CH$_3$), 1.18 (10-CH$_3$), 1.07 (4-CH$_3$), 1.06 (8-CH$_3$), 0.90 (15-CH$_3$). $^{13}$C NMR (75 MHz, CDCl$_3$) δ 178.4 (C-9), 177.2 (C-1), 153.9 (C=O carbonate), 102.7 (C-1'), 94.0 (C-1"), 84.7 (C-12), 83.6 (C-11), 79.1 (C-5), 78.7 (C-6), 77.9 (C-4"), 75.5 (C-3), 75.2 (C-13), 72.6 (C-3"), 70.7 (C-2'), 68.5 (C-5'), 65.3 (C-5"), 65.1 (C-3'), 51.0 (6-OCH$_3$), 49.2 (3"-OCH$_3$), 44.9 (C-2), 44.3 (C-10), 42.0 (C-4), 40.1/3'-N(CH$_3$)$_2$/, 39.4 (C-7), 36.2 (C-8), 34.3 (C-2"), 28.6 (C-4'), 21.8 (C-14), 21.3 (3"-CH$_3$), 21.1 (5'-CH$_3$), 21.0 (6-CH$_3$), 19.6 (8-CH$_3$), 18.0 (5"-CH$_3$), 14.1 (2-CH$_3$), 13.0 (10-CH$_3$), 12.8 (12-CH$_3$), 10.2 (15-CH$_3$), 9.1 (4-CH$_3$).

EXAMPLE 2

3-Decladinosyl-3-oxy-6-O-methyl-9a-aza-9a-homoerythromycin A 11,12-Cyclic Carbonate In 0.25 N hydrochloric acid (45 ml) the substance from the Example 1 (1.5 g, 0.002 mole) was dissolved and it was left standing at room temperature for 48 hours. Onto the reaction mixture $CH_2Cl_2$ (30 ml, pH 1.5) was added, the pH of the mixture was adjusted with conc. $NH_4OH$ to pH 9.0, the layers were separated and the aqueous one was extracted two more times with $CH_2Cl_2$ (30 ml). The combined organic extracts were rinsed with 10% aqueous $NaHCO_3$ solution and water and evaporated, yielding 3-decladinosyl-3-oxy-6-O-methyl-9a-aza-9a-homoerythromycin A 11,12-cyclic carbonate (1.1 g)

IR (KBr) cm$^{-1}$ 3440, 2974, 2939, 1822, 1729, 1650, 1525, 1457, 1380, 1241, 1167, 1113, 1073, 1047, 983. FAB-MS m/z 731 (MH$^+$).

EXAMPLE 3

2'-O-Acetyl-3-decladinosyl-3-oxy-6-O-methyl-9a-aza-9a-homoerythromycin A 11,12-Cyclic Carbonate To a solution of 3-decladinosyl-3-oxy-6-O-methyl-9a-aza-9a-homoerythromycin A 11,12-cyclic carbonate from the Example 2 (1.0 g, 0.0016 mole) in $CH_2Cl_2$ (100 ml), $NaHCO_3$ (0.62 g, 0.0074 mole) and acetic acid anhydride (0.36 ml, 0.0038 mole) were added and it was then stirred for 4 hours at room temperature. Onto the reaction mixture a saturated $NaHCO_3$ solution (50 ml) was added, the layers were separated and the aqueous one was extracted two more times with $CH_2Cl_2$ (20 ml). The combined organic extracts were rinsed with a saturated $NaHCO_3$ solution and water and evaporated, yielding the title product (1.15 g) with the following physical-chemical constants:

IR (KBr) cm$^{-1}$ 3444, 2975, 2936, 1816, 1737, 1666, 1539, 1461, 1376, 1237, 1166, 1113, 1046, 1015, 985, 943. $^1$H NMR (300 MHz, CDCl$_3$) δ 6.97 (9a-CONS), 4.97 (H-13), 4.80 (H-2'), 4.69 (H-1'), 4.29 (H-11), 4.27 (H-10), 3.89 (H-5), 3.62 (H-3), 3.53 (H-5'), 3.22 (6-OCH$_3$), 2.87 (H-3'), 2.74 (H-2), 2.30/3'-N(CH$_3$)$_2$/, 2.30 (H-8), 1.98 (H-4), 1.81 (H-7a), 1.86 (H-14a), 1.78 (H-4'a), 1.64 (H-14b), 1.41*(12-CH$_3$), 1.35 (H-4'b), 1.30 (2-CH$_3$), 1.30 (H-7b), 1.29*(6-CH$_3$), 1.26 (5'-CH$_3$), 1.19 (10-CH$_3$), 1.12 (8-CH$_3$), 0.94 (4-CH$_3$), 0.92 (15-CH$_3$). $^{13}$C NMR (75 MHz, CDCl$_3$) δ 178.4 (C-1)*, 177.2 (C-9)*, 170.0 (2'-COCH$_3$), 153.3 (C=O carbonate), 99.3 (C-1'), 85.5 (C-12), 83.8 (C-11), 79.6 (C-6), 78.8 (C-5), 76.9 (C-13), 76.5 (C-3), 70.9 (C-2'), 68.5 (C-5'), 62.5 (C-3'), 50.2 (6-OCH$_3$), 43.9 (C-2), 43.8 (C-10), 39.9/3'-N(CH$_3$)$_2$/, 38.9 (C-7), 36.7 (C-4), 34.1 (C-8), 30.8 (C-4'), 21.7 (C-14), 20.8 (5'-CH$_3$), 21.1 (2'-CONH$_3$), 19.1 (6-CH$_3$), 18.1 (8-CH$_3$), 17.5 (10-CH$_3$), 15.4 (2-CH$_3$), 12.2 (12-CH$_3$), 10.0 (15-CH$_3$), 7.7 (4-CH$_3$).

EXAMPLE 4

3-Decladinosyl-3-oxo-6-O-methyl-9a-aza-9a-homoerythromycin A 11,12-Cyclic Carbonate To a solution of 2'-O-acetyl-3-decladinosyl-3-oxy-6-O-methyl-9a-aza-9a-homo-erythromycin A 11,12-cyclic carbonate from the Example 3 (1 g, 0.0015 mole) in $CH_2Cl_2$ (20 ml), dimethyl sulfoxide (2.5 ml) and N,N-dimethylaminopropyl-ethyl-carbodiimide (2.64 g, 0.014 mole) were added. The reaction mixture was cooled to 15° C. and then, under stirring and maintaining the temperature, a pyridinium trifluoroacetate solution (2.7 g, 0.014 mole) in $CH_2Cl_2$ (12 ml) was gradually added drop by drop during 1 hour. The temperature of the reaction mixture was gradually raised to room temperature, it was kept stirring for further 4 hours and the reaction was ceased by the addition of a saturated NaCl solution (20 ml) and $CH_2Cl_2$ (20 ml). After alkalizing to pH 9.5 (2N NaOH), the reaction mixture was extracted with $CH_2Cl_2$ and the organic extracts were rinsed with a saturated NaCl solution and water and dried over $K_2CO_3$. After filtration and evaporation of methylene chloride at a reduced pressure, an oily residue was obtained, which was subjected to methanolysis (70 ml) for 24 hours at room temperature. Methanol was evaporated at a reduced pressure and the obtained residue was purified by low-pressure chromatography on a silica gel column using chloroform and then the solvent system CHCl$_3$—CH$_3$OH-conc.NH$_4$OH, 6:1:0.1. By evaporation of chromatographically homogeneous fractions, the title product (0.2 g) with the following physical-chemical constants was obtained:

IR (KBr) cm$^{-1}$ 3442, 3380, 2975, 2940, 2881, 2840, 2787, 1813, 1750, 1717, 1666, 1586, 1526, 1458, 1381, 1325, 1237, 1166, 1111, 1079, 1050, 1017, 991, 957. $^1$H NMR (300 MHz, CDCl$_3$) δ 6.39 (9a-CONH), 4.96 (H-13), 4.44 (H-1'), 4.34 (H-10), 4.21 (H-11), 4.14 (H-5), 3.94 (H-2), 3.60 (H-5'), 3.27 (H-4), 3.20 (H-2'), 2.85 (6-OCH$_3$), 2.50 (H-3'), 2.27/3'-N(CH$_3$)$_2$/, 2.27 (H-8), 2.27 (H-7a), 1.84 (H-14a), 1.67 (H-4'a), 1.62 (H-14b), 1.52 (6-CH$_3$), 1.45 (2-CH$_3$), 1.45 (H-7b), 1.34 (4-CH$_3$), 1.27 (12-CH$_3$), 1.24 (5'-CH$_3$), 1.23 (H-4'b), 1.22 (10-CH$_3$), 1.12 (8-CH$_3$), 0.91 (15-CH$_3$). $^{13}$C NMR (75 MHz, CDCl$_3$) δ 206.7 (C-3), 177.0 (C-9)*, 170.1*(C-1), 153.6 (C=O carbonate), 103.4 (C-1'), 84.4 (C-12), 84.1 (C-11), 78.5 (C-5), 78.1 (C-6), 75.7 (C-13), 70.1 (C-2'), 69.2 (C-5'), 65.4 (C-3'), 50.1 (6-OCH$_3$), 50.0 (C-2), 47.7 (C-4), 44.2 (C-10), 39.9/3'-N(CH$_3$)$_2$/, 39.1 (C-7), 36.2 (C-8), 28.0 (C-4'), 21.7 (C-14), 20.9 (5'-CH), 20.5 (12-CH$_3$), 19.8 (8-CH$_3$), 16.3 (2-CH$_3$), 14.8 (4-CH$_3$), 13.6 (10-CH$_3$), 13.0 (6-CH$_3$), 10.0 (15-CH$_3$).

EXAMPLE 5

3-Decladinosyl-3-oxy-6-O-methyl-9a-aza-9a-homoerythromycin A 11,12-Cyclic Carbonate By a reaction of 3-decladinosyl-3-oxy-6-O-methyl-9a-aza-9a-homoerythromycin A and ethylene carbonate according to the process described in the Example 1, 3-decladinosyl-3-oxy-6-O-methyl-9a-aza-9a-homoerythromycin A 11,12-cyclic carbonate with the physical-chemical constants as given in the Example 2 was obtained.

EXAMPLE 6

3-Decladinosyl-3-O-(4-nitrophenyl)acetyl-6-O-methyl-9a-aza-9a-homoerythromycin A 11,12-Cyclic Carbonate To a solution of 4-nitrophenyl acetic acid (0.263 g, 0.0015 mole) in dry $CH_2Cl_2$ (5 ml), triethylamine (0.202 ml, 0.0015 mole) was added and it was cooled to 0° C. To the reaction mixture pivaloyl chloride (0.180 ml, 0.0015 mole) was added, it was stirred for 30 minutes at the same temperature and then pyridine (0.4 ml) and a solution of 2'-O-acetyl-3-decladinosyl-3-oxy-6-O-methyl-9a-aza-9a-homoerythromycin A 11,12-cyclic carbonate from the Example 3 (0.3 g, 0.0004 mole) were added. It was stirred at the same temperature for further 3 hours, to the reaction mixture a saturated NaCl solution (20 ml) was added, the layers were separated and the aqueous one was extracted two more times with $CH_2Cl_2$ (20 ml). The combined organic extracts were dried over $K_2CO_3$ and evaporated at a reduced pressure. Onto the oily residue methanol (30 ml) was added and it was left standing at room temperature over night. Methanol was evaporated at a reduced pressure and the obtained residue was purified by chromatography on a silica gel column using the system $CH_2Cl_2$—$CH_3OH$-conc.$NH_4OH$, 90:4:0.5 and by crystallisation from a mixture methylene chloride-ether-(n-hexane), whereby a chromatographically homogeneous title product was obtained.

IR (KBr) cm$^{-1}$ 3417, 3380, 2975, 2939, 1813, 1750, 1742, 1669, 1524, 1526, 1458, 1348, 1167, 1076, 1046.

EXAMPLE 7

3-Decladinosyl-3-O-(4-nitrophenyl)acetyl-6-O-methyl-9a-aza-9a-homoerythromycin A By reacting 2'-O-acetyl-3-decladinosyl-3-oxy-6-O-methyl-9a-aza-9a-homoerythromycin A (0.3 g, 0.0004 mole) obtained according to the process described in PCT/HR 99/00004, 4/99, 4-nitrophenyl acetic acid (0.263 g, 0.0015 mole) and pivaloyl chloride (0.180 ml, 0.015 mole), there was obtained according to the process described in the Example 6, a chromatographically homogeneous title product with the following physical-chemical constants:

IR (KBr) cm$^{-1}$ 3396, 2976, 2941, 2879, 2791, 1732, 1698, 1669, 1601, 1521, 1456, 1380, 1346, 1232, 1182, 1111, 1073, 1051, 983. FAB-MS m/z 768 (MH$^+$).

EXAMPLE 8

3-Decladinosyl-3,11-dioxo-6-O-methyl-9a-aza-9a-homoerythromycin A

To a solution of 2'-O-acetyl-3-decladinosyl-3-oxy-6-O-methyl-9a-aza-9a-homoerythromycin A (0.760 g, 0.0012 mole) obtained according to the process described in PCT/HR 99/00004, 4/99, in $CH_2Cl_2$ (25 ml), dimethyl sulfoxide (2.5 ml) and N,N-dimethyl-aminopropyl-ethyl-carbodiimide (2.7 g, 0.014 mole) were added. The reaction mixture was cooled to 15° C. and then, under stirring and maintaining the temperature, gradually drop by drop a solution of pyridinium trifluoroacetate (2.75 g, 0.0014 mole) in $CH_2Cl_2$ (10 ml) was added over 45 minutes. The temperature of the reaction mixture was gradually raised to room temperature, the mixture was stirred for further 10 hours and then the reaction was ceased by the addition of a saturated NaCl solution (25 ml) and $CH_2Cl_2$ (25 ml). After alkalizing with 2 N NaOH to pH 9.5, the reaction mixture was extracted with $CH_2Cl_2$, the organic extracts were subsequently rinsed with a saturated NaCl solution, $NaHCO_3$ and water and dried over $K_2CO_3$. After filtration and evaporation of $CH_2Cl_2$ at a reduced pressure, a product (1.2 g) was obtained. The oily residue was subjected to methanolysis (50 ml) for 24 hours at room temperature. Methanol was evaporated at a reduced pressure and the obtained residue was purified by low-pressure chromatography on a silica gel column using the system ethyl acetate-(n-hexane)-diethyl amine, 10:10:2. By evaporation of chromatographically homogeneous fractions with lower Rf and by rechromatography in the system $CH_2Cl_2$—$CH_3OH$-conc.$NH_4OH$, 90:9:0.5, a chromatographically homogeneous title product with the following physical-chemical constants was obtained:

IR (KBr) cm$^{-1}$ 3291, 2975, 2940. 2879, 2788, 1732, 1715. 1661. 1557, 1457, 1378, 1339, 1300, 1264, 1174, 1110, 1079, 1051, 1010, 982. $^1$H NMR(300 MHz, CDCl$_3$) δ 7.57 (9a-CONH), 5.05 (H-10), 4.85 (H-13), 4.62 (H-5), 4.35 (H-1'), 3.77 (H-2), 3.65 (H-5'), 3.47 (H-4), 3.23 (H-2'), 3.09 (6-OCH$_3$), 2.57 (H-8), 2.57 (H-7a), 2.50 (H-3'), 2.28/3'-N(CH$_3$)$_2$/, 2.02 (H-14a), 1.72 (10-CH$_3$), 1.70 (H-4'a), 1.58 (H-14b), 1.43 (H-7b), 1.38 (4-CH$_3$), 1.33*(6-CH$_3$), 1.31 (2-CH$_3$), 1.28 (5'-CH$_3$), 1.22*(12-CH$_3$), 1.21 (H-4'b), 1.11 (8-CH$_3$), 0.89 (15-CH$_3$). $^{13}$C NMR (75 MHz, CDCl$_3$) δ 211.0 (C-11), 208.5 (C-3), 179.0 (C-9)*, 172.4*(C-1), 102.8 (C-1'), 79.6*(C-12), 79.1 (C-6), 76.7 (C-13), 73.8 (C-5), 70.0 (C-2'), 69.1 (C-5'), 65.5 (C-3'), 53.6 (C-10) 49.2 (6-OCH$_3$), 48.5 (C-2), 44.9 (C-4), 40.0/3'N(CH$_3$)$_2$/, 38.8 (C-7), 32.7 (C-8), 28.2 (C-4'), 21.1 (5'-CH$_3$), 20.4 (C-14), 18.8(12-CH$_3$), 18.6(6-CH$_3$), 17.7 (8-CH$_3$), 16.1 (10-CH$_3$), 14.3 (4-CH$_3$), 13.3 (2-CH$_3$), 10.5-CH$_3$). FAB-MS m/z 601 (MH$^+$).

EXAMPLE 9

3-Decladinosyl-3-oxy-6-O-methyl-8a-aza-8a-homoerythromycin A 11,12-Cyclic Carbonate To ethyl acetate (15 ml) there were added 3-decladinosyl-3-oxy-6-O-methyl-8a-aza-8a-homoerythromycin A (1.9 g, 0.0031 mole) obtained according to the process described in PCT/HR 99/00004, 4/99, $K_2CO_3$ (2.5 g, 0.0018 mole) and ethylene carbonate (5.5 g, 0.063 mole), and then the reaction mixture was stirred for 10 hours at the temperature 90° C. To the reaction mixture again ethylene carbonate (2.5 g) was added and it was stirred for further 7 hours at the same temperature. Into the cooled reaction mixture water (30 ml) was added, the layers were separated and the aqueous one was extracted with $CH_2Cl_2$ (2×30 ml). The combined organic extracts were dried over $K_2CO_3$ and evaporated under reduced pressure, yielding a crude residue (2.5 g). By chromatography on a silica gel column using the system $CH_2Cl_2$—$CH_3OH$-conc.$NH_4OH$, 90:4:0.5, a chromatographically homogenous title product (1.3 g) was obtained.

IR (KBr) cm$^{-1}$ 3444, 2975, 2940, 2833, 1817, 1733, 1651, 1545, 1461, 1384, 1340, 1235, 1165, 1111, 1082, 1049. $^1$H NMR (600 MHz, CDCl$_3$) δ 5.90 (8a-CONH), 5.27 (H-13), 4.53 (H-11), 4.40 (H-1'), 3.99 (H-3), 3.88 (H-5), 3.77 (H-8), 3.55 (H-5'), 3.24 (H-2'), 3.12 (6-OCH$_3$), 2.60 (H-2), 2.51 (H-10), 2.49 (H-3'), 2.26/3'-N(CH$_3$)$_2$/, 1.76 (H-14a), 1.70 (H-7a), 1.67 (H-4'a), 1.67 (H-14b), 1.65 (H-7b), 1.61 (H-4), 1.37 (12-CH$_3$), 1.34 (10-CH$_3$), 1.32 (6-CH$_3$), 1.30 (2-CH$_3$), 1.29 (8-CH$_3$), 1.26 (5'-CH$_3$), 1.25 (H-4'b), 1.01 (4-CH$_3$), 0.93 (15-CH$_3$). $^{13}$C NMR (150 MHz, CDCl$_3$) δ 175.5 (C-1), 170.4 (C-9), 153.1 (C=O carbonate), 106.9 (C-1'), 91.7 (C-5), 86.8 (C-12), 82.9 (C-11), 79.1 (C-6), 76.8 (C-3), 74.8 (C-13), 70.4 (C-2'), 69.8 (C-5'), 65.5 (C-3'), 49.3 (6-OCH$_3$), 43.9 (C-2), 43.8 (C-8), 42.5 (C-10), 41.1 (C-7), 40.2/3'-N (CH$_3$)$_2$/, 37.1 (C-4), 28.1 (C-4'), 22.2 (C-14), 21.7 (8-CH$_3$), 21.3 (6-CH$_3$), 20.8 (5'-CH$_3$), 16.3 (12-CH$_3$), 15.6 (2-CH$_3$), 14.8 (10-CH$_3$), 10.2 (15-CH$_3$), 7.9 (4-CH$_3$). FAB-MS m/z 631 (MH$^+$).

EXAMPLE 10

2'-O-Acetyl-3-decladinosyl-3-oxy-6-O-methyl-8a-aza-8a-homoerythromycin A 11,12-Cyclic Carbonate To a mixture of solvents $CH_2Cl_2$ (10 ml) and acetone (1 ml), 3-decladinosyl-3-oxy-6-O-methyl-8a-aza-8a-homoerythromycin A 11,12-cyclic carbonate (0.75 g, 0.0012 mole) from the Example 9, $NaHCO_3$ (0.5 g, 0.0059 mole) and acetic acid anhydride (0.28 ml, 0.003 mole) were added and it was stirred for 3 hours at room temperature. To the reaction mixture a saturated $NaHCO_3$ solution (10 ml) was added, the layers were separated and the aqueous layer was extracted with $CH_2Cl_2$ (2×20 ml). The combined organic extracts were rinsed with a saturated NaCl solution, dried over $K_2CO_3$ and evaporated at a reduced pressure, yielding the title product (0.8 g).

IR (KBr) cm$^{-1}$ 3389, 2975, 2940, 1813, 1741, 1659, 1540, 1458, 1374, 1237, 1166, 1058. $^1$H NMR (600 MHz, CDCl$_3$) δ 6.22 (8a-CONH), 5.16 (H-13), 4.78 (H-2'), 4.63 (H-1'), 4.53 (H-11), 3.89 (H-8), 3.84 (H-5), 3.83 (H-3), 3.54 (H-5'), 3.13 (6-OCH$_3$), 2.87 (H-3'), 2.61 (H-2), 2.49 (H-10), 2.30/3'-N(CH$_3$)$_2$/, 2.09 (COCH$_3$), 1.82 (H-14a), 1.80 )H-7a), 1.78 (H-4'a), 1.75 (H-4), 1.64 (H-14b), 1.60 (H-7b), 1.39 (12-CH$_3$), 1.36 (H-4'b), 1.32 (10-CH$_3$), 1.28 (2-CH$_3$), 1.26 (6-CH$_3$), 1.26 (5'-CH$_3$), 1.23 (8-CH$_3$), 0.92 (15-CH$_3$), 0.91 (4-CH$_3$). $^{13}$C NMR (150 MHz, CDCl$_3$) δ 174.7 (C-1), 170.6 (C-9), 170.3 (COCH$_3$), 153.2 (C=O carbonate), 101.5 (C-1'), 86.3 (C-5), 85.5 (C-12), 82.4 (C-11), 78.6 (C-6), 76.0 (C-3), 75.5 (C-13), 71.3 (C-2'), 68.8 (C-5'), 63.0 (C-3'), 49.9 (6-OCH$_3$), 43.8 (C, 2), 42.5 (C-8), 42.4 (C-10), 41.1 (C-7), 40.0/3'-N(CH$_3$)$_2$/, 37.7 (C-4), 30.5 (C-4'), 22.1 (C-8), 22.1 (C-14), 21.4 (6-CH$_3$), 21.2 (COCH$_3$), 21.0 (5'-CH$_3$), 15.7 (12-CH$_3$), 15.3 (2-CH$_3$), 13.9 (10-CH$_3$), 10.1 (4-CH$_3$), 8.2 (15-CH$_3$).

EXAMPLE 11

3-Decladinosyl-3-O-(4-nitrophenyl)acetyl-6-O-methyl-8a-aza-8a-homoerythromycin A 11,12-Cyclic Carbonate By reacting 2'-O-acetyl-3-decladinosyl-3-oxy-6-O-methyl-8a-aza-8a-homo-erythromycin A 11,12-cyclic carbonate (0.3 g, 0.0004 mole) obtained according to the process described in the Example 10,4-nitrophenyl acetic acid (0.263 g, 0.0015 mole) and pivaloyl chloride (0.180 ml, 0.0015 mole), according to the process described in the Example 6, a chromatographically homogeneous title product with the following physical-chemical constants was obtained:

IR (KBr) cm$^{-1}$ 3437, 2976, 2940, 1809, 1666, 1524, 1459, 1348, 1233, 1166, 1111. $^1$H NMR (600 MHz, CDCl$_3$) δ 8.20 and 7.52 (Ph), 6.19 (8a-CONH), 5.47 (H-3), 5.01 (H-13), 4.47 (H-11), 4.05 (H-1'), 3.92 (H-8), 3.84 and 3.80 (PhCH$_2$), 3.74 (H-5), 3.30 (H-5'), 3.20 (6-OCH$_3$), 3.16 (H-2'), 2.83 (H-2), 2.48 (H-10), 2.38 (H-3'), 2.28/3'-N(CH$_3$)$_2$/, 2.09 (COCH$_3$), 2.07 (H-4), 1.86 (H-14a), 1.83 (H-7a), 1.63 (H-4'a), 1.61 (H-14b), 1.55 (H-7b), 1.44 (12-CH$_3$), 1.31 (10-CH$_3$), 1.30 (6-CH$_3$), 1.19 (H-4'b), 1.20 (5'-CH$_3$), 1.24 (8-CH$_3$), 1.02 (2-CH$_3$), 0.91 (15-CH$_3$), 0.8 (4-CH$_3$). $^{13}$C NMR (150 MHz, CDCl$_3$) δ 173.5*(C-1), 170.8*(C-9), 169.8*(3-OCOCH$_2$—), 153.1 (C=O carbonate), 147.2, 141.2, 130.5, 123.7 (Ph), 103.9 (C-1'). 85.9 (C-12), 82.4 (C-5), 82.0 (C-11), 79.0 (C-6), 76.7 (C-3), 76.0 (C-13), 70.3 (C-2'), 69.6 (C-5'), 65.9 (C-3'), 50.7 (6-OCH$_3$), 43.8 (C-2), 43.1 (C-10), 43.0 (C-8), 41.7 CH$_2$Ph), 40.3/3'-N(CH$_3$)$_2$/, 38.4 (C-4), 28.3 (C-4'), 22.3 (8-CH$_3$), 22.3 (C-14), 21.3 (6-CH$_3$), 21.1 (5'-CH$_3$), 15.0 (12-CH$_3$), 14.2 (2-CH$_3$), 13.8 (10-CH$_3$), 10.6 (4-CH$_3$), 10.2 (15-CH$_3$). FAB-MS m/z 794 (MH$^+$).

EXAMPLE 12

3-Decladinosyl-3-O-(4-nitrophenyl)acetyl-6-O-methyl-8a-aza-8a-homoerythromycin A By reacting 2'-O-acetyl-3-decladinosyl-3-oxy-6-O-methyl-8a-aza-8a-homoerythromycin A (0.3 g, 0.0004 mole) obtained according to the process described in PCT/HR 99/00004, 4/99, 4-nitrophenyl acetic acid (0.263 g, 0.0015 mole), pivaloyl chloride (0.180 ml, 0.0015 mole) and triethylamine (0.202 ml, 0.0015 mole), according to the process described in the Example 6, a chromatographically homogeneous title product with the following physical-chemical constants was obtained:

IR (KBr) cm$^{-1}$ 3440, 2976, 2937, 1741, 1651, 1525, 1461, 1348, 1168, 1076, 1050. FAB-MS m/z 768 (MH$^+$). $^1$H NMR (600 MHz, CDCl$_3$) δ 8.20 (d, Ph), 7.54 (Ph), 5.91 (8a-CONH), 5.38 (H-3), 5.03 (H-13), 3.96 (H-1'), 3.87 (PhCH$_2$), 3.82 (H-8), 3.81 (PhCH$_2$), 3.74 (H-5), 3.42 (H-11), 3.25 (H-5'), 3.19 (H-2'), 3.19 (6-OMe), 2.77 (H-2), 2.38 (H-10), 2.33 (H-3'), 2.27/3'-N(CH$_3$)$_2$/, 2.14 (H-4), 1.92 (H-14a), 1.86 (H-7a), 1.60 (H-4'a), 1.51 (H-7b), 1.47 (H- 14b), 1.29 (6-CH$_3$), 1.24 (8-CH$_3$), 1.19 (10-CH$_3$), 1.19 (H-4'b), 1.18 (5'-CH$_3$), 1.13 (4-CH$_3$), 1.10 (12-CH$_3$), 0.92 (2-CH$_3$), 0.84 (15-CH$_3$). $^{13}$C NMR (150 MHz, CDCl$_3$) δ 174.9 (C-9), 174.7 (C-1), 169.7 (3-OCOCH$_2$—), 147.2, 141.1, 130.4, 123.7 (Ph), 104.1 (C-1'), 83.3 (C-5), 78.7 (C-3), 78.6 (C-13), 77.5 (C-6), 74.8 (C-12), 70.5 (C-11), 70.4 (C-2'), 69.6 (C-5'), 66.1 (C-3'), 51.0 (6-OCH$_3$), 43.2 (C-2), 42.9 (C-10), 42.6 (C-8), 42.2 (C-7), 41.3 (-CH$_2$Ph), 40.3/3'-N(CH$_3$)$_2$/, 37.1 (C-4), 28.3 (C-4'), 23.1 (8-CH$_3$), 21.3 (C-14), 21.1 (5'-CH$_3$), 20.9 (6-CH$_3$), 16.3 (12-CH$_3$), 15.6 (2-CH$_3$), 10.8 (15-CH$_3$), 10.1 (10-CH$_3$), 9.53 (4-CH$_3$).

EXAMPLE 13

3-Decladinosyl-3-O-(4-chlorophenyl)acetyl-6-O-methyl-8a-aza-8a-homoerythromycin A 11,12-Cyclic Carbonate By reacting 2'-O-acetyl-3-decladinosyl-3-oxy-6-O-methyl-8a-aza-8a-homoerythromycin A 11,12-cyclic carbonate (0.2 g, 0.0003 mole) obtained according to the process described in the Example 10, 4-chlorophenyl acetic acid (0.330 g, 0.0019 mole), pivaloyl chloride (0.239 ml, 0.0019 mole) and triethyl amine (0.270 ml, 0.0019 mole) over 3 days at room temperature according to the process described in the Example 6, a chromatographically homogenous title product with the following physical-chemical constants was obtained:

IR (KBr) cm$^{-1}$ 3388, 2976, 2941, 2883, 2787, 1812, 1744, 1667, 1541, 1493, 1458, 1380, 1357, 1332, 1234, 1165, 1111, 1051, 1017, 981. FAB-MS m/z 783 (MH$^+$).

EXAMPLE 14

3-Decladinosyl-3-O-(4-methoxyphenyl)acetyl-6-O-methyl-8a-aza-8a-homoerythromycin A By reacting 2'-O-acetyl-3-decladinosyl-3-oxy-6-O-methyl-8a-aza-8a-homoerythromycin A (0.250 g, 0.0004 mole) obtained according to the process described in PCT/HR 99/00004, 4/99, 4-methoxyphenyl acetic acid (0.321 g, 0.0019 mole), pivaloyl chloride (0.239 ml, 0.0019 mole) and triethylamine (0.270 ml, 0.0019 mole) over 5 days at room temperature according to the process described in the Example 6, a chromatographically homogeneous title product was obtained:

IR (KBr) cm$^{-1}$ 3444, 2975, 2939, 2836, 2787, 1740, 1651, 1514, 1462, 1379, 1337, 1257, 1167, 1110, 1076, 1035, 984, 959. FAB-MS m/z 753 (MH$^+$).

EXAMPLE 15

3-Decladinosyl-3-oxo-6-O-methyl-8a-aza-8a-homoerythromycin A 11,12-Cyclic Carbonate To a solution of 2'-O-acetyl-3-decladinosyl-3-oxy-6-O-methyl-8a-aza-8a-homoerythromycin A 11,12-cyclic carbonate from the Example 10 (0.4 g, 0.00059 mole) in CH$_2$Cl$_2$ (20 ml) dimethyl sulfoxide (0.7 ml) and N,N-dimethyl-aminopropyl-ethyl-carbodiimide (0.7 g, 0.0036 mole) were added. The reaction mixture was cooled to 15°

C., under stirring and maintaining the temperature a solution of pyridinum trifluoroacetate (0.7 g, 0.0036 mole) in $CH_2Cl_2$ (5 ml) was added drop by drop over 15 minutes, the temperature of the reaction mixture was raised to room temperature and the reaction was kept stirring over night. After the addition of a saturated NaCl solution (30 ml) and $CH_2Cl_2$ (30 ml), the reaction mixture was alkalized to pH 10 (2 N NaOH) and extracted with $CH_2Cl_2$. The organic extracts were rinsed with a saturated NaCl solution and water, dried over $K_2CO_3$ and evaporated at a reduced pressure, yielding 0,5 g of an oily residue, which was subjected to methanolysis (30 ml) at room temperature for 24 hours. Methanol was evaporated at a reduced pressure, the obtained residue (0.49 g) was purified by low-pressure chromatography on a silica gel column using chloroform and then solvent system $CH_2Cl_2$—$CH_3OH$-conc.$NH_4OH$, 90:4:0.5 yielding a chromatographically homogeneous title product with the following physical-chemical constants:

IR (KBr) $cm^{-1}$ 3379, 2976, 1814, 1755, 1713, 1668, 1539, 1457, 1381, 1243, 1166, 1110, 1062, 995. FAB-MS m/z 629 ($MH^+$).

What is claimed is:

1. A compound of formula (I),

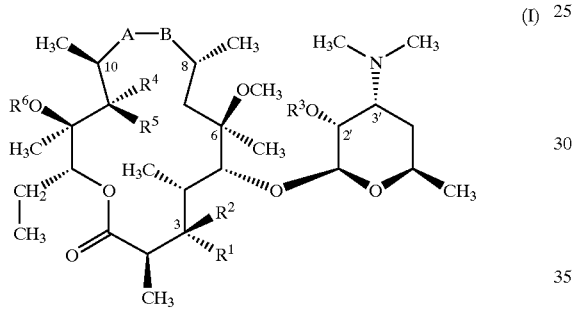

(I)

or its pharmaceutically acceptable addition salts with inorganic or organic acids or hydrates thereof, wherein A stands for NH group and B simultaneously stands for C=O group, or A stands for C=O group and B simultaneously stands for NH group, $R^1$ stands for OH group, L-cladinosyl group of formula (II),

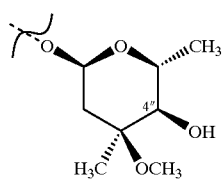

$R^1$ stands for a group of formula (III),

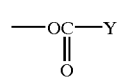

(III)

wherein

Y stands for hydrogen, $C_1$–$C_6$ alkyl, $C_1$–$C_6$ alkyl group with at least one incorporated O, N or S atom or Y stands for $(CH_2)_n$—Ar, wherein $(CH_2)_n$ stands for alkyl and n is 1–10, with or without incorporated O, N or S atoms, and Ar stands for a 5–10-membered monocyclic or bicyclic aromatic ring containing 0–3 O, N or S atoms, which is unsubstituted or substituted with 1–3 groups representing halogen, OH, OMe, $NO_2$, $NH_2$, amino-$C_1$–$C_3$ alkyl or amino-$C_1$–$C_3$ dialkyl, CN, $SO_2NH_2$, $C_1$–$C_3$ alkyl, or $R^1$ together with $R^2$ stands for oxo, $R^2$ stands for hydrogen or together with $R^1$ stands for oxo, $R^3$ stands for hydrogen or $C_1$–$C_4$ alkanoyl group, $R^4$ stands for hydrogen or together with $R^5$ stands for oxo, $R^5$ stands for OH, $NH_2$, amino-$C_1$–$C_3$ alkyl or amino-$C_1$–$C_3$ dialkyl, $O(CH_2)_n$Ar or $S(CH_2)_n$Ar, wherein $(CH_2)_n$ and Ar have the above meanings, or together with $R^4$ stands for oxo, with proviso that when $R^5$ stands for OH, $R^1$ does not stand for L-cladinosyl group of formula (II) or OH, $R^6$ stands for hydrogen, $C_1$–$C_6$ alkyl, hetero $C_1$–$C_6$ alkyl group wherein said hetero atom is O, N or S, or $(CH_2)_n$—Ar group, wherein $(CH_2)_n$ and Ar have the above meanings, with proviso that when $R^6$ stands for H, $R^1$ does not stand for L-cladinosyl group of formula (II) or OH, or $R^5$ and $R^6$ together with intervening atoms form an additional ring of formula (IV)

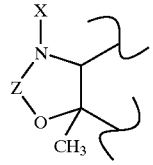

(IVa)

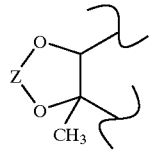

(IVb)

wherein

Z stands for $CH_2$, C=O, C(NH), SO, $SO_2$, $CH_2CO$, $COCH_2$, $CH_2CH_2CO$, $COCH_2CH_2$ or $CH_2CH_2$, and X stands for hydrogen, $C_1$–$C_3$ alkyl, $NH_2$, amino-$C_1$–$C_3$ alkyl or amino-$C_1$–$C_3$ dialkyl or $(CH_2)_n$—Ar group, wherein $(CH_2)_n$ and Ar have the above meanings.

2. A compound according to claim 1, characterized in that A stands for NH and B simultaneously stands for C=O group, $R^1$ stands for L-cladinosyl group of formula (II) and $R^2$, $R^3$ and $R^4$ are mutually the same and stand for hydrogen, $R^5$ and $R^6$ together with intervening atoms form an additional ring of formula (IV), wherein Z stands for $CH_2$, C=O, C(NH), SO, $SO_2$, $CH_2CO$, $COCH_2$, $CH_2CH_2CO$, $COCH_2CH_2$ or $CH_2CH_2$, and X stands for hydrogen, $C_1$–$C_3$ alkyl, $NH_2$, amino-$C_1$–$C_3$ alkyl or amino-$C_1$–$C_3$ dialkyl or $(CH_2)_n$—Ar group, wherein $(CH_2)_n$ and Ar have the meanings given in claim 1.

3. A compound according to claim 2, characterized in that A stands for NH group and B simultaneously stands for C=O group, $R^1$ stands for L-cladinosyl group of formula (II) and $R^2$, $R^3$ and $R^4$ are mutually the same and stand for hydrogen, $R^5$ and $R^6$ together with intervening atoms form an additional ring of formula (IVb), wherein Z stands for C=O group.

4. A compound according to claim 1, characterized in that A stands for C=O group and B simultaneously stands for NH group, $R^1$ stands for L-cladinosyl group of formula (II) and $R^2$, $R^3$ and $R^4$ are mutually the same and stand for hydrogen, $R^5$ and $R^6$ together with intervening atoms form an additional ring of formula (IV), wherein Z stands for $CH_2$, $C=O$, $C(NH)$, SO, $SO_2$, $CH_2CO$, $COCH_2$, $CH_2CH_2CO$, $COCH_2CH_2$ or $CH_2CH_2$, and X stands for hydrogen, $C_1$–$C_3$ alkyl, $NH_2$, amino-$C_1$–$C_3$ alkyl or amino-$C_1$–$C_3$ dialkyl or $(CH_2)_n$—Ar group, wherein $(CH_2)_n$ and Ar have the meanings given in claim 1.

5. A compound according to claim 4, characterized in that A stands for $C=O$ group and B simultaneously stands for NH group, $R^1$ stands for L-cladinosyl group of formula (II) and $R^2$, $R^3$ and $R^4$ are mutually the same and stand for hydrogen, $R^5$ and $R^6$ together with intervening atoms form an additional ring of formula (IVb), wherein Z stands for $C=O$ group.

6. A compound according to claim 1, characterized in that A stands for NH group and B simultaneously stands for $C=O$ group, $R^1$ stands for OH and $R^2$, $R^3$ and $R^4$ are mutually the same and stand for hydrogen, $R^5$ and $R^6$ together with intervening atoms form an additional ring of formula (IV), wherein Z stands for $CH_2$, $C=O$, $C(NH)$, SO, $SO_2$, $CH_2CO$, $COCH_2$, $CH_2CH_2CO$, $COCH_2CH_2$ or $CH_2CH_2$, and X stands for hydrogen, $C_1$–$C_3$ alkyl, $NH_2$, amino-$C_1$–$C_3$ alkyl or amino-$C_1$–$C_3$-dialkyl or $(CH_2)_n$—Ar group, wherein $(CH_2)_n$ and Ar have the meanings given in claim 1.

7. A compound according to claim 6, characterized in that A stands for NH group and B simultaneously stands for $C=O$ group, $R^1$ stands for OH and $R^2$, $R^3$ and $R^4$ are mutually the same and stand for hydrogen, $R^5$ and $R^6$ together with intervening atoms form an additional ring of formula (IVb), wherein Z stands for $C=O$ group.

8. A compound according to claim 1, characterized in that A stands for NH group and B simultaneously stands for $C=O$ group, $R^1$ stands for OH, and $R^2$ and $R^4$ are mutually the same and stand for hydrogen, $R^3$ stands for $C_1$–$C_4$ alkanoyl group, $R^5$ and $R^6$ together with intervening atoms form an additional ring of formula (IVb), wherein Z stands for $C=O$ group.

9. A compound according to claim 8, characterized in that A stands for NH group and B simultaneously stands for $C=O$ group, $R^1$ stands for OH, and $R^2$ and $R^4$ are mutually the same and stand for hydrogen, $R^3$ stands for acetyl group, $R^5$ and $R^6$ together with intervening atoms form an additional ring of formula (IVb), wherein Z stands for $C=O$ group.

10. A compound according to claim 1, characterized in that A stands for $C=O$ group and B simultaneously stands for NH group, $R^1$ stands for OH and $R^2$, $R^3$ and $R^4$ are mutually the same and stand for hydrogen, $R^5$ and $R^6$ together with intervening atoms form an additional ring of formula (IV), wherein Z stands for $CH_2$, $C=O$, $C(NH)$, SO, $SO_2$, $CH_2CO$, $COCH_2$, $CH_2CH_2CO$, $COCH_2CH$, or $CH_2CH_2$, and X stands for hydrogen, $C_1$–$C_3$ alkyl, $NH_2$, amino-$C_1$–$C_3$ alkyl or amino-$C_1$–$C_3$-dialkyl or $(CH_2)_n$—Ar group, wherein $(CH_2)_n$ and Ar have the meanings given in claim 1.

11. A compound according to claim 10, characterized in that A stands for $C=O$ group and B simultaneously stands for NH group, $R^1$ stands for OH and $R^2$, $R^3$ and $R^4$ are mutually the same and stand for hydrogen, $R^5$ and $R^6$ together with intervening atoms form an additional ring of formula (IV), wherein Z stands for $C=O$ group.

12. A compound according to claim 1, characterized in that A stands for $C=O$ group and B simultaneously stands for NH group, $R^1$ stands for OH, $R^2$ and $R^4$ are mutually the same and stand for hydrogen, $R^3$ stands for $C_1$–$C_4$ alkanoyl group, $R^5$ and $R^6$ together with intervening atoms form an additional ring of formula (IVb), wherein Z stands for $C=O$ group.

13. A compound according to claim 12, characterized in that A stands for $C=O$ group and B simultaneously stands for NH group, $R^1$ stands for OH, $R^2$ and $R^4$ are mutually the same and stand for hydrogen, $R^3$ stands for acetyl group, $R^5$ and $R^6$ together with intervening atoms form an additional ring of formula (IVb), wherein Z stands for $C=O$ group.

14. A compound according to claim 1, characterized in that A stands for NH group and B simultaneously stands for $C=O$ group, $R^1$ stands for a group of formula (III), wherein Y stands for hydrogen, $C_1$–$C_6$ alkyl, $C_1$–$C_6$ alkyl group with at least one incorporated O, N or S atom, or Y stands for $(CH_2)_n$—Ar, wherein $(CH_2)$, stands for alkyl and n is 1–10, without or with incorporated O, N or S atoms, and Ar stands for a 5–10-membered monocyclic or bicyclic aromatic ring comprising 0–3 O, N or S atoms which is unsubstituted or substituted with 1–3 groups representing halogen, OH, OMe, $NO_2$, $NH_2$, amino-$C_1$–$C_3$ alkyl or amino-$C_1$–$C_3$ dialkyl, CN, $SO_2NH_2$, $C_1$–$C_3$ alkyl, $R^2$, $R^3$ and $R^4$ are mutually the same and stand for hydrogen, $R^5$ and $R^6$ together with intervening atoms form an additional ring of formula (IV), wherein Z stands for $CH_2$, $C=O$, $C(NH)$, SO, $SO_2$, $CH_2CO$, $COCH_2$, $CH_2CH_2CO$, $COCH_2CH_2$ or $CH_2CH_2$, and X stands for hydrogen, $C_1$–$C_3$ alkyl, $NH_2$, amino-$C_1$–$C_3$ alkyl or amino-$C_1$–$C_3$ dialkyl or $(CH_2)_n$—Ar group, wherein $(CH_2)_n$ and Ar have the above meanings.

15. A compound according to claim 14, characterized in that A stands for NH group and B simultaneously stands for $C=O$ group, $R^1$ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-$NO_2$ group, $R^2$, $R^3$ and $R^4$ are mutually the same and stand for hydrogen, $R^5$ and $R^6$ together with intervening atoms form an additional ring of formula (IVb), wherein Z stands for $C=O$.

16. A compound according to claim 14, characterized in that A stands for NH group and B simultaneously stands for $C=O$ group, $R^1$ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-$OCH_3$ group, $R^2$, $R^3$ and $R^4$ are mutually the same and stand for hydrogen, $R^5$ and $R^6$ together with intervening atoms form an additional ring of formula (IVb), wherein Z stands for $C=O$.

17. A compound according to claim 14, characterized in that A stands for NH group and B simultaneously stands for $C=O$ group, $R^1$ stands for a group of formula (III) wherein Y stands for $(CH_2)_n$—Ar, wherein $(CH_2)_n$ stands for alkyl and n is 1 and Ar stands for a 6-membered monocyclic aromatic ring substituted with p-$NH_2$ group, $R^2$, $R^3$ and $R^4$ are mutually the same and stand for hydrogen, $R^5$ and $R^6$ together with intervening atoms form an additional ring of formula (IVb), wherein Z stands for $C=O$.

18. A compound according to claim 14, characterized in that A stands for NH group and B simultaneously stands for $C=O$ group, $R^1$ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-OH group, $R^2$, $R^3$ and $R^4$ are mutually the same and stand for hydrogen, $R^5$ and $R^6$ together with intervening atoms form an additional ring of formula (IVb), wherein Z stands for $C=O$.

19. A compound according to claim 14, characterized in that A stands for NH group and B simultaneously stands for C=O group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-Cl, R², R³ and R⁴ are mutually the same and stand for hydrogen, R⁵ and R⁶ together with intervening atoms form an additional ring of formula (IVb), wherein Z stands for C=O.

20. A compound according to claim 14, characterized in that A stands for NH group and B simultaneously stands for C=O group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-SO₂NH₂, R², R³ and R⁴ are mutually the same and stand for hydrogen, R⁵ and R⁶ together with intervening atoms form an additional ring of formula (IVb), wherein Z stands for C=O.

21. A compound according to claim 14, characterized in that A stands for NH group and B simultaneously stands for C=O group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-NH—(CH₃) group, R², R³ and R⁴ are mutually the same and stand for hydrogen, R⁵ and R⁶ together with intervening atoms form an additional ring of formula (IVb), wherein Z stands for C=O.

22. A compound according to claim 14, characterized in that A stands for NH group and B simultaneously stands for C=O group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-N(CH₃)₂ group, R², R³ and R⁴ are mutually the same and stand for hydrogen, R⁵ and R⁶ together with intervening atoms form an additional ring of formula (IVb), wherein Z stands for C=O.

23. A compound according to claim 14, characterized in that A stands for NH group and B simultaneously stands for C=O group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-CH₃ group, R², R³ and R⁴ are mutually the same and stand for hydrogen, R⁵ and R⁶ together with intervening atoms form an additional ring of formula (IVb), wherein Z stands for C=O.

24. A compound according to claim 1, characterized in that A stands for C=O group and B simultaneously stands for NH group, R¹ stands for a group of formula (III), Y stands for hydrogen, $C_1$–$C_6$ alkyl, $C_1$–$C_6$ alkyl group with at least one incorporated O, N or S atom, or Y stands for $(CH_2)_n$—Ar, wherein $(CH_2)_n$ stands for alkyl and n is 1–10, without or with incorporated O, N or S atoms, and Ar stands for 5–10-membered monocyclic or bicyclic aromatic ring comprising 0–3 O, N or S atoms which is unsubstituted or substituted with 1–3 groups representing halogen, OH, OMe, NO₂, NH₂, amino-$C_1$–$C_3$ alkyl or amino-$C_1$–$C_3$ dialkyl, CN, SO₂NH₂, $C_1$–$C_3$ alkyl, R², R³ and R⁴ are mutually the same and stand for hydrogen, R⁵ and R⁶ together with intervening atoms form an additional ring of formula (IV), wherein Z stands for CH₂, C=O, C(NH), SO, SO₂, CH₂CO, COCH₂, CH₂CH₂CO, COCH₂CH, or CH₂CH₂, and X stands for hydrogen, $C_1$–$C_3$ alkyl, NH₂ amino-$C_1$–$C_3$ alkyl or amino-$C_1$–$C_3$ dialkyl or $(CH_2)_n$—Ar group, wherein $(CH_2)_n$ and Ar have the above meanings.

25. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-NO₂ group, R², R³ and R⁴ are mutually the same and stand for hydrogen, R⁵ and R⁶ together with intervening atoms form an additional ring of formula (IVb), wherein Z stands for C=O.

26. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-OCH₃ group, R², R³ and R⁴ are mutually the same and stand for hydrogen, R⁵ and R⁶ together with intervening atoms form an additional ring of formula (IVb), wherein Z stands for C=O.

27. A compound according to claim 24, characterized in that A stands for C=O group and B simultaneously stands for NH group, R¹ stands for a group of formula (III) wherein Y stands for $(CH_2)_n$—Ar, wherein $(CH_2)N$ stands for alkyl and n is 1 and Ar stands for 6-membered monocyclic aromatic ring substituted with p-NH₂ group, R², R³ and R⁴ are mutually the same and stand for hydrogen, R⁵ and R⁶ together with intervening atoms form an additional ring of formula (IVb), wherein Z stands for C=O.

28. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-OH group, R², R³ and R⁴ are mutually the same and stand for hydrogen, R⁵ and R⁶ together with intervening atoms form an additional ring of formula (IVb), wherein Z stands for C=O.

29. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-Cl, R², R³ and R⁴ are mutually the same and stand for hydrogen, R⁵ and R⁶ together with intervening atoms form an additional ring of formula (IVb), wherein Z stands for C=O.

30. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-SO₂NH₂, R², R³ and R⁴ are mutually the same and stand for hydrogen, R⁵ and R⁶ together with intervening atoms form an additional ring of formula (IVb), wherein Z stands for C=O.

31. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-NH—(CH₃) group, R², R³ and R⁴ are mutually the same and stand for hydrogen, R⁵ and R⁶ together with intervening atoms form an additional ring of formula (IVb), wherein Z stands for C=O.

32. A compound according to claim 24, characterized in that A stands for C=O group and B simultaneously stands for NH group, R¹ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-N(CH₃)₂ group, R², R³ and R⁴ are mutually the same and stand for hydrogen, R⁵ and R⁶ together with intervening atoms form an additional ring of formula (IVb), wherein Z stands for C=O.

33. A compound according to claim 24, characterized in that A stands for C=O group and B simultaneously stands for NH group, $R^1$ stands for a group of formula (III) wherein Y stands for $(CH_2)_n$—Ar, wherein $(CH_2)_n$ stands for alkyl and n is 1 and Ar stands for 6-membered monocyclic aromatic ring substituted with p-$CH_3$ group, $R^2$, $R^3$ and $R^4$ are mutually the same and stand for hydrogen, $R^5$ and $R^6$ together with intervening atoms form an additional ring of formula (IVb), wherein Z stands for C=O.

34. A compound according to claim 1, characterized in that A stands for NH group and B simultaneously stands for C=O group, $R^1$ has the meaning of the group of the formula (III), wherein Y stands for hydrogen, $C_1$–$C_6$ alkyl, $C_1$–$C_6$ alkyl group with at least one incorporated O, N or S atom, or Y stands for $(CH_2)_n$—Ar, wherein $(CH_2)_n$ stands for alkyl and n stands for 1–10, without or with incorporated O, N or S atoms, and Ar stands for 5–10-membered monocyclic or bicyclic aromatic ring containing 0–3 O, N or S atoms, which is unsubstituted or substituted with 1–3 groups representing halogen, OH, OMe, $NO_2$, $NH_2$, amino-$C_1$–$C_3$ alkyl or amino-$C_1$–$C_3$ dialkyl, CN, SO, $NH_2$, $C_1$–$C_3$ alkyl, $R^2$, $R^3$, $R^4$, and $R^6$ are mutually the same and stand for hydrogen and $R^5$ is OH group.

35. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$NO_2$ group, $R^2$, $R^3$, $R^4$, and $R^6$ are mutually the same and stand for hydrogen and $R^5$ is OH.

36. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$OCH_3$ group, $R^2$, $R^3$, $R^4$, and $R^6$ are mutually the same and stand for hydrogen and $R^5$ is OH.

37. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$NH_2$ group, $R^2$, $R^3$, $R^4$, and $R^6$ are mutually the same and stand for hydrogen and $R^5$ is OH.

38. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-OH group, $R^2$, $R^3$, $R^4$, and $R^6$ are mutually the same and stand for hydrogen and $R^5$ is OH.

39. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-Cl, $R^2$, $R^3$, $R^4$, and $R^6$ are mutually the same and stand for hydrogen and $R^5$ is OH.

40. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$SO_2NH_2$, $R^2$, $R^3$, $R^4$, and $R^6$ are mutually the same and stand for hydrogen and $R^5$ is OH.

41. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-NH—$CH_3$ group, $R^2$, $R^3$, $R^4$, and $R^6$ are mutually the same and stand for hydrogen and $R^5$ is OH.

42. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-N$(CH_3)_2$ group, $R^2$, $R^3$, $R^4$, and $R^6$ are mutually the same and stand for hydrogen and $R^5$ is OH.

43. A compound according to claim 34, characterized in that A stands for NH group and B simultaneously stands for C=O group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$CH_3$ group, $R^2$, $R^3$, $R^4$, and $R^6$ are mutually the same and stand for hydrogen and $R^5$ is OH.

44. A compound according to claim 1, characterized in that A stands for C=O group and B simultaneously stands for NH group, $R^1$ has the meaning of the group of the formula (III), wherein Y stands for hydrogen, $C_1$–$C_6$ alkyl, $C_1$–$C_6$ alkyl group with at least one incorporated O, N or S atom, or Y stands for $(CH_2)_n$—Ar, wherein $(CH_2)_n$ stands for alkyl and n stands for 1–10, without or with incorporated O, N or S atoms, and Ar stands for 5–10-membered monocyclic or bicyclic aromatic ring containing 0–3 O, N or S atoms, which is unsubstituted or substituted with 1–3 groups representing halogen, OH, OMe, $NO_2$, $NH_2$, amino-$C_1$–$C_3$ alkyl or amino-$C_1$–$C_3$ dialkyl, CN, $SO_2NH_2$, $C_1$–$C_3$ alkyl, $R^2$, $R^4$, and $R^6$ are mutually the same and stand for hydrogen and $R^5$ is OH group.

45. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$NO_2$ group, $R^2$, $R^3$, $R^4$, and $R^6$ are mutually the same and stand for hydrogen and $R^5$ is OH.

46. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$OCH_3$ group, $R^2$, $R^3$, $R^4$, and $R^6$ are mutually the same and stand for hydrogen and $R^5$ is OH.

47. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$NH_2$ group, $R^2$, $R^3$, $R^4$, and $R^6$ are mutually the same and stand for hydrogen and $R^5$ is OH.

48. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-OH group, $R^2$, $R^3$, $R^4$, and $R^6$ are mutually the same and stand for hydrogen and $R^5$ is OH.

49. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-Cl, $R^2$, $R^3$, $R^4$, and $R^6$ are mutually the same and stand for hydrogen and $R^5$ is OH.

50. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$SO_2NH_2$, $R^2$, $R^3$, $R^4$, and $R^6$ are mutually the same and stand for hydrogen and $R^5$ is OH.

51. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-NH—$CH_3$ group, $R^2$, $R^3$, $R^4$, and $R^6$ are mutually the same and stand for hydrogen and $R^5$ is OH.

52. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-N$(CH_3)_2$ group, $R^2$, $R^3$, $R^4$, and $R^6$ are mutually the same and stand for hydrogen and $R^5$ is OH.

53. A compound according to claim 44, characterized in that A stands for C=O group and B simultaneously stands for NH group, $R^1$ has the meaning of the group of the formula (III), wherein Y stands for $(CH_2)_n$—Ar, wherein $(CH_2)_n$ stands for alkyl and n stands for 1 and Ar stands for 6-membered monocyclic aromatic ring substituted with p-$CH_3$ group, $R^2$, $R^3$, $R^4$, and $R^6$ are mutually the same and stand for hydrogen and $R^5$ is OH.

54. A compound according to claim 1, characterized in that A stands for NH group and B simultaneously stands for C=O group, $R^1$ and $R^2$ together stand for a ketone, $R^3$ and $R^6$ are mutually the same and stand for hydrogen and $R^4$ and $R^5$ together stand for a ketone.

55. A compound according to claim 1, characterized in that A stands for C=O group and B simultaneously stands for NH group, $R^1$ and $R^2$ together stand for a ketone, $R^3$ and $R^6$ are mutually the same and stand for hydrogen and $R^4$ and $R^5$ together stand for a ketone.

56. A compound according to claim 1, characterized in that A stands for NH group and B simultaneously stands for C=O group, $R^1$ and $R^2$ together stand for a ketone, $R^3$ and $R^4$ are mutually the same and stand for hydrogen, $R^5$ and $R^6$ together with intervening atoms form an additional ring of formula (IV), wherein Z stands for $CH_2$, C=O, C(NH), SO, $SO_2$, $CH_2CO$, $COCH_2$, $CH_2CH_2CO$, $COCH_2CH_2$ or $CH_2CH_2$, and X stands for hydrogen, $C_1$-$C_3$ alkyl, $NH_2$, amino-$C_1$-$C_3$ alkyl or amino-$C_1$-$C_3$ dialkyl or $(CH_2)_n$—Ar group, wherein $(CH_2)_2$ and Ar have the meanings given in claim 1.

57. A compound according to claim 56, characterized in that A stands for NH group and B simultaneously stands for C=O group, $R^1$ and $R^2$ together stand for a ketone, $R^3$ and $R^4$ are mutually the same and stand for hydrogen, $R^5$ and $R^6$ together with intervening atoms form an additional ring of formula (IVb), wherein Z stands for C=O.

58. A compound according to claim 1, characterized in that A stands for C=O group and B simultaneously stands for NH group, $R^1$ and $R^2$ together stand for a ketone, $R^3$ and $R^4$ are mutually the same and stand for hydrogen, $R^5$ and $R^6$ together with intervening atoms form an additional ring of formula (IV), wherein Z stands for $CH_2$, C=O, C(NH), SO, $SO_2$, $CH_2CO$, $COCH_2$, $CH_2CH_2CO$, $COCH_2CH_2$ or $CH_2CH_2$, and X stands for hydrogen, $C_1$-$C_3$ alkyl, $NH_2$, amino-$C_1$-$C_3$ alkyl or amino-$C_1$-$C_3$ dialkyl or $(CH_2)_n$—Ar group, wherein $(CH_2)_n$ and Ar have the meanings given in claim 1.

59. A compound according to claim 1, characterized in that A stands for C=O group and B simultaneously stands for NH group, $R^1$ and $R^2$ together stand for a ketone, $R^3$ and $R^4$ are mutually the same and stand for hydrogen, $R^5$ and $R^6$ together with intervening atoms form an additional ring of formula (IVb), wherein Z stands for C=O.

60. A process for preparation of a compound of formula (I),

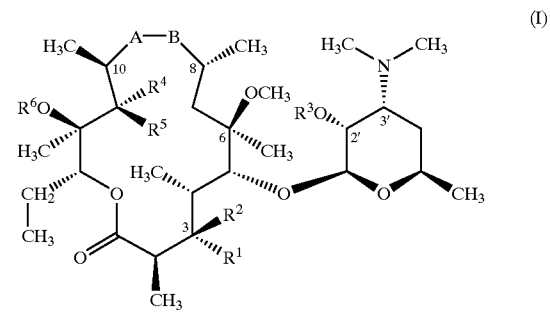

or its pharmaceutically acceptable addition salts, with inorganic or organic acids, or hydrates thereof, wherein
  A stands for NH group and B simultaneously stands for C=O group, or
  A stands for C=O group and B simultaneously stands for NH group,
  $R^1$ stands for OH group, L-cladinosyl group of formula (II),

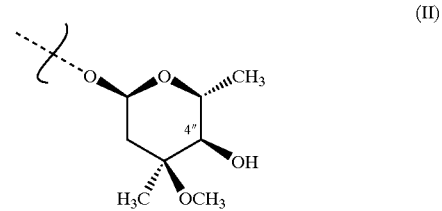

or $R^1$ stands for a group of formula (III),

wherein
  Y stands for hydrogen, $C_1$-$C_6$ alkyl, $C_1$-$C_6$ alkyl group with at least one incorporated O, N or S atom or Y stands for (CH$_2$)$_n$—Ar, wherein (CH$_2$)$_n$, stands for alkyl and n stands for 1–10, with or without incorporated O, N or S atoms, and Ar stands for 5–10-membered monocyclic or bicyclic aromatic ring containing 0–3 O, N or S atoms, which is unsubstituted or substituted with 1–3 groups representing halogen, OH, OMe, NO$_2$, NH$_2$, amino-C$_1$–C$_3$ alkyl or amino-C$_1$–C$_3$ dialkyl, CN, SO$_2$NH$_2$, C$_1$–C$_3$ alkyl, or R$^1$ together with R$^2$ stands for oxo, R$^2$ stands for hydrogen or together with R$^1$ stands for oxo, R$^3$ stands for hydrogen or C$_1$–C$_4$ alkanoyl group, R$^4$ stands for hydrogen or together with R$^5$ stands for oxo, R$^5$ stands for OH, NH$_2$, amino-C$_1$–C$_3$ alkyl or amino-C$_1$–C$_3$ dialkyl, O(CH$_2$)$_n$Ar or S(CH$_2$)$_n$Ar, wherein (CH$_2$)$_n$ and Ar have the above meanings, or together with R$^4$ stands for oxo, with proviso that when R$^5$ stands for OH, R$^1$ does not stand for L-cladinosyl group of formula (II) or OH, R$^6$ stands for hydrogen, C$_1$–C$_6$ alkyl, hetero C$_1$–C$_6$ alkyl group wherein said hetero atom is O, N or S, or (CH$_2$)$_n$—Ar group, wherein (CH$_2$)$_n$ and Ar have the above meanings, with proviso that when R$^6$ stands for H, R$^1$ does not stand for L-cladinosyl group of formula (II) or OH, or R$^5$ and R$^6$ together with intervening atoms form an additional ring of formula (IV)

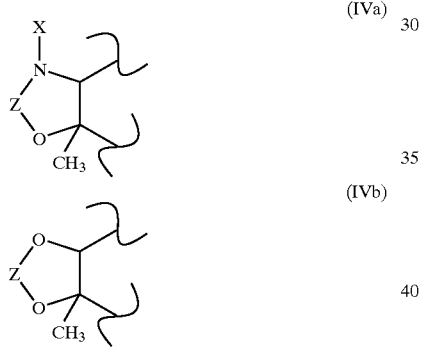

wherein

Z stands for CH$_2$, C=O, C(NH), SO, SO$_2$, CH$_2$CO, COCH$_2$, CH$_2$CH$_2$CO, COCH$_2$CH$_2$ or CH$_2$CH$_2$, and X stands for hydrogen, C$_1$–C$_3$ alkyl, NH$_2$, amino-C$_1$–C$_3$ alkyl or amino-C$_1$–C$_3$ dialkyl or (CH$_2$)$_n$—Ar group, wherein (CH$_2$)$_n$ and Ar have the above meanings, characterized in that, A/
a) 6-O-methyl-9a-aza-9a-homoerythromycin A or 6-O-methyl-8a-aza-8a-homoerythromycin A of the general formula (I), wherein A stands for NH group and B simultaneously stands for C=O group, or A stands for C=O group and B simultaneously stands for NH group, R$^1$ stands for L-cladinosyl group of the formula (II) and R$^2$, R$^3$, R$^4$ and R$^6$ are mutually the same and stand for hydrogen and R$^5$ stands for OH group, obtained according to PCT/HR 99/00004, 4/99, are subjected to a reaction with ethylene carbonate in the presence of inorganic or organic bases, preferably potassium carbonate, in a reaction-inert solvent, preferably in ethyl acetate, yielding corresponding 11,12-cyclic carbonates of the general formula (I), wherein A stands for NH group and B simultaneously stands for C=O group, or A stands for C=O group and B simultaneously stands for NH group, R$^1$ stands for L-cladinosyl group of the formula (II) and R$^2$, R$^3$ and R$^4$ are mutually the same and stand for hydrogen, R$^5$ and R$^6$ together with intervening atoms form an additional ring of the formula (IVb), wherein Z stands for C=O group, which are subsequently subjected to b) hydrolysis with strong acids, preferably with 0.25–1.5 N hydrochloric acid, in a mixture of water and lower alcohols, preferably methanol, ethanol or isopropanol, over 10–30 hours at room temperature, yielding 3-decladinosyl derivatives of the general formula (I), wherein A stands for NH group and B simultaneously stands for C=O group, or A stands for C=O group and B simultaneously stands for NH group, R$^1$ stands for OH group, R$^2$, R$^3$ and R$^4$ are mutually the same and stand for hydrogen, and R$^5$ and R$^6$ together with intervening atoms form an additional ring of the formula (IVb), wherein Z stands for C=O group, which are subsequently subjected to c) a selective acylation of a hydroxyl group in 2'-position with chlorides or anhydrides of carboxylic acids with up to 4 carbon atoms, preferably with acetic acid anhydride, in the presence of inorganic or organic bases such as sodium hydrogen carbonate, sodium carbonate, potassium carbonate, triethyl amine, pyridine, tributylamine, preferably sodium hydrogen carbonate, in a reaction-inert solvent such as methylene chloride, dichloroethane, acetone, pyridine, ethyl acetate, tetrahydrofuran, preferably methylene chloride, at a temperature from 0–30° C., yielding 2'-O-acyl derivatives of the general formula (I), wherein A stands for NH group and B simultaneously stands for C=O group, or A stands for C=O group and B simultaneously stands for NH group, R$^1$ stands for OH group, R$^2$ and R$^4$ are mutually the same and stand for hydrogen, R$^3$ stands for acetyl and R$^5$ and R$^6$ together with intervening atoms form an additional ring of formula (IVb), wherein Z stands for C=O group, which are optionally subjected to d1) a reaction with mixed anhydrides of carboxylic acids of formula Y—COO—R', wherein Y stands for hydrogen, C$_1$–C$_6$ alkyl, hetero C$_1$–C$_6$ alkyl group wherein said hetero atom is O, N or S, or Y stands for (CH$_2$)$_n$—Ar, wherein (CH$_2$)$_n$ stands for alkyl and n is 1–10, without or with incorporated O, N or S atoms, and Ar stands for 5–10-membered monocyclic or bicyclic aromatic ring comprising 0–3 O, N or S atoms which is unsubstituted or substituted with 1–3 groups representing halogen, OH, OMe, NO$_2$, NH$_2$, amino-C$_1$–C$_3$ alkyl or amino-C$_1$–C$_3$ dialkyl, CN, SO$_2$NH$_2$, C$_1$–C$_3$ alkyl and R$^1$ represents a group which is usually used for the preparation of mixed anhydrides such as pivaloyl, p-toluenesulfonyl, isobutoxycarbonyl, ethoxycarbonyl or isopropoxycarbonyl groups, in the presence of inorganic or organic bases, in a reaction-inert solvent, preferably in methylene chloride, at a temperature from 0–30° C. over 3–100 hours, yielding 3-acyl derivatives of the general formula (I), wherein R$^1$ stands for a group of formula (III), Y has the above meanings, A stands for NH group and B simultaneously stands for C=O group, or A stands for C=O group and B simultaneously stands for NH group, R$^2$ and R$^4$ are mutually the same and stand for hydrogen, $R^3$ stands for acetyl and $R^5$ and $R^6$ together with intervening atoms form an additional ring of formula (IVb), wherein Z stands for C=O group, which are subsequently subjected to deprotection with lower alcohols, preferably in methanol, at a temperature from room temperature to the reflux temperature of the solvent, yielding a compound of the general formula (I), wherein R3 stands for hydrogen and all remaining substituents have the above meanings, or to d2) oxidation of a hydroxyl group in C-3 position of the aglycone ring according to a modified Moffat-Pfitzner process with N-N-dimethyl aminopropyl-3-ethyl-carbodiimide in the presence of dimethyl sulfoxide and pyridinium trifluoroacetate as catalyst, in an inert organic solvent, preferably in methylene chloride, at a temperature from 10° C. to room temperature, yielding 3-oxo derivatives of the general formula (I), wherein A stands for NH group and B simultaneously stands for C=O group, or A stands for C=O group and B simultaneously stands for NH group, $R^1$ together with $R^2$ stands for oxo, $R^3$ stands for acetyl group, $R^4$ stands for hydrogen and $R^5$ and $R^6$ together with intervening atoms form an additional ring of formula (IVb), wherein Z stands for C=O group, which are subsequently subjected to deprotection in lower alcohols, preferably in methanol, at a temperature from room temperature to the reflux temperature of the solvent, yielding a compound of the general formula (I), wherein $R^3$ stands for hydrogen and all remaining substituents have the above meanings, or B/
a) 6-O-methyl-9a-aza-9a-homoerythromycin A or 6-O-methyl-8a-aza-8a-homoerythromycin A of the general formula (I), wherein A stands for NH group and B simultaneously stands for C=O group, or A stands for C=O group and B simultaneously stands for NH group, $R^1$ stands for L-cladinosyl group of the formula (II) and $R^2$, $R^3$, $R^4$ and $R^6$ are mutually the same and stand for hydrogen and $R^5$ stands for OH group, obtained according to PCT/HR 99/00004, 4/99, are subjected to hydrolysis with strong acids, then to a selective acylation of 2'-position, which are then optionally subjected to b1) a reaction with mixed anhydrides and deprotection as given above, yielding a compound of the general formula (I), wherein $R^1$ has the meaning of a group of the formula (III), wherein Y stands for hydrogen, $C_1$–$C_6$ alkyl, hetero $C_1$–$C_6$ alkyl group wherein said hetero atom is O, N or S, or Y stands for $(CH_2)_n$—Ar, wherein $(CH_2)_n$ stands for alkyl and n is 1–10, without or with incorporated O, N or S atoms, and Ar stands for a 5–10-membered monocyclic or bicyclic aromatic ring containing 0–3 O, N or S atoms, which is unsubstituted or substituted with 1–3 groups representing halogen, OH, OMe, $NO_2$, $NH_2$, amino-$C_1$–$C_3$ alkyl or amino-$C_1$–$C_3$ dialkyl, CN, $SO_2NH_2$, $C_1$–$C_3$ alkyl, $R^2$, $R^3$, $R^4$, and $R^6$ are mutually the same and stand for hydrogen and $R^5$ is OH group, or to b2) oxidation of hydroxyl groups in C-3 and C-11 positions of an aglycone ring according to a modified Moffat-Pfitzner process as given above, and deprotection, yielding a compound of the general formula (I), wherein A stands for NH group and B simultaneously stands for C=O group, or A stands for C=O group and B simultaneously stands for NH group, $R^1$ together with $R^2$ stands for an oxo, $R^3$ and $R^6$ are mutually the same and stand for hydrogen and $R^4$ together with $R^5$ stands for an oxo, or alternatively, compounds obtained according to the process Ad1) can be prepared by subjecting the compounds from the step Bb1) to a reaction with ethylene carbonate in a manner as described in Aa), or alternatively, compounds from the step Ab) can be obtained by changing the sequence of the reaction steps in such a manner that 6-O-methyl-9a-aza-9a-homoerythromycin A or 6-O-methyl-8a-aza-8a-homoerythromycin A obtained according to PCT/HR 99/00004, 4/99, are first subjected to hydrolysis with strong acids as described in Ab) and then to a reaction with ethylene carbonate in a manner described in Aa), or alternatively, the compounds from Ad2) can be obtained in such a manner that 3-decladinosyl-3-oxo-6-O-methyl-9a-aza-9a-homoerythromycin A or 3-decladinosyl-3-oxo-6-O-methyl-8a-aza-8a-homoerythromycin A, obtained according to PCT/HR 99/00004, 4/99, are subjected to a reaction with ethylene carbonate in a manner described in the step Aa), and for obtaining their pharmaceutically acceptable addition salts, the novel compounds from the class of 6-O-methyl-9a-aza-9a-homo- and 6-O-methyl-8a-aza-8a-homoerythromycins A of the general formula (I), wherein A, B, $R^1$, $R^2$, $R^3$, $R^4$, $R^5$ and $R^6$ have the above meanings, are reacted with an at least equimolar amount of a suitable inorganic or organic acid such as hydrochloric, hydroiodic, sulfuric, phosphoric, acetic, propionic, trifluoroacetic, maleic, citric, stearic, succinic, ethylsuccinic, methanesulfonic, benzenesulfonic, p-toluenesulfonic, laurylsulfonic acid and the like, in a reaction-inert solvent, and by isolating by means of filtration if they are insoluble in the reaction-inert solvent, or precipitation by means of a non-solvent or of evaporation of the solvent, most frequently by lyophilization.

61. Pharmaceutical composition useful for treatment of bacterial infections in humans and animals comprising therapeutically effective amounts of a compound of formula (I) or its pharmaceutically acceptable addition salts according to claim 1, in combination with a pharmaceutically acceptable carrier.

62. Method for treating bacterial infections in humans and animals comprising administering to humans and animals required therapeutically effective amounts of a compound of the formula (I) or pharmaceutically acceptable addition salts thereof according to claim 1, in combination with a pharmaceutically acceptable carrier.

* * * * *